United States Patent
Svadovskiy

(10) Patent No.: US 6,918,935 B2
(45) Date of Patent: Jul. 19, 2005

(54) METHOD FOR RADICAL REMOVAL OF PARASAGITTAL MENINGIOMA

(76) Inventor: Aleksandr Igorevich Svadovskiy, kv.24, d.4-2 ul., Bolshaya Cherkizovskaya, Moscow 105187 (RU)

( * ) Notice: Subject to any disclaimer, the term of this patent is extended or adjusted under 35 U.S.C. 154(b) by 354 days.

(21) Appl. No.: 10/065,844

(22) Filed: Nov. 25, 2002

(65) Prior Publication Data

US 2003/0105507 A1 Jun. 5, 2003

(51) Int. Cl.[7] ............................. A61F 2/36; A61B 19/00
(52) U.S. Cl. ..................................... 623/23.64; 128/898
(58) Field of Search ............................. 623/1.15–1.22, 623/1.27, 1.35, 1.44–1.54, 9, 10, 23.64–23.7

(56) References Cited

U.S. PATENT DOCUMENTS

| | | | | |
|---|---|---|---|---|
| 5,429,582 A | * | 7/1995 | Williams | 600/2 |
| 5,693,097 A | * | 12/1997 | Laguette et al. | 623/9 |
| 6,254,638 B1 | * | 7/2001 | Schouwenburg | 623/9 |

* cited by examiner

Primary Examiner—Corrine McDermott
Assistant Examiner—Hieu Phan
(74) Attorney, Agent, or Firm—Ronald E. Smith; Smith & Hopen, P.A.

(57) ABSTRACT

The present invention relates to medicine and more particularly to neurosurgery, and can be used in the operative treatment of patients with parasagittal meningiomas. The present invention is directed to the provision of radical removal of a parasagittal meningioma, restoring and securing natural blood flow, obviating recurrent parasagittal meningioma. The object is accomplished by that semicircular incisions of the dura mater circumscribing the tumor contour are made toward the base of the upper sagittal sinus, the tumor is removed as a single block together with a segment of the upper sagittal sinus and a portion of the faix cerebri, whereafter the removed segment of the upper sagittal sinus is replaced with an implant prosthesis ensuring physiological blood flow. The prosthesis is a cynlindrical tubular member in which the end parts are provided with smooth, curvilinear, gently sloping bevels made on its internal generating surface or on both internal and external surfaces thereof.

4 Claims, 1 Drawing Sheet

METHOD FOR RADICAL REMOVAL OF PARASAGITTAL MENINGIOMA

BACKGROUND OF THE INVENTION

CROSS-REFERENCE TO RELATED DISCLOSURE

The present application is a continuation application claiming the benefit of prior filed Russian application, serial number RU 2001/132542, filed Dec. 3, 2001.

BACKGROUND OF THE INVENTION

The present invention relates to medicine and more particularly to neurosurgery, and can be used in the operative treatment of patients with parasagittal meningiomas.

Parasagittal meninglomas (PSM) are a kind of meningioma whose initial growth point is, as a rule, a side wall of the upper sagittal sinus (USS), less frequently the tumor is anatomically connected with the falx cerebri. PSMs constitute about one half of all meningiomas. Usually PSM grows with the node outwards from the wall of the sinus, crushing the adjacent brain but not growing through it. Another direction of the PSM growth Is the USS lumen till the latter becomes completely obturated and the tumor extends to the opposite side.

Known in the art is a method for removing a parasagittal meningioma (see Irger I. M., "Neirokhirurgiya", Moscow, 1972 (in Russian)). This method employs bi/monopolar electrocauterizing of the starting region of the tumor growth (matrix which is usually located on the side wall of the upper sagittal sinus).

However, this method leads to perforation of the side wall of the USS, to development of massive hemorrhage, and also to recurrent tumor.

A method for removing a parasagittal meningioma is also known (see Gabibov G. O., Ph.D. thesis "Clinical Picture, Diagnosis and Surgical Treatment of Parasagittal Meningiomas", Moscow, 1967 (in Russian)), which comprises carrying out osteoplastic trepanation and opening of the dura mater in the projection of the tumor location.

This method is disadvantageous in that the tumor Is removed mechanically as large fragments or piece-wise, which may cause abundant hemorrhage.

USS ligation in the course of the operation (particularly In the middle and rear third thereof) often leads to serious complications (postoperative lethality with the tumor located in the middle third of the USS is 9.8%; with the tumor located in the rear third of the USS, 33.3%), and even to lethal outcomes (according to the data reported by different authors, the total postoperative lethality after the removal of PSM varies from 14 to 27%). USS ligation in the front third thereof is relatively safe. Here lethal outcomes are caused by venous hyperemia with subsequent development of venous infarctions, edema of the brain, dislocation and displacement of the truncus cerebri (so-called "wedging-in").

BRIEF DESCRIPTION OF DRAWINGS

For a fuller understanding of the nature and objects of the invention, reference should be made to the following detailed description, taken in connection with the accompanying drawings, in which.

DETAILED DESCRIPTION

It is an object of the present invention to provide radical removal of parasagittal meningioma, restoring and securing natural blood flow, obviating recurrent parasagittal meningioma.

Said object is accomplished by that semicircular incisions of the dura mater circumscribing the tumor contour are made toward the base of the upper sagittal sinus, the tumor is removed as a single block together with a segment of the upper sagittal sinus and a portion of the falx cerebri, whereafter the removed segment of the upper sagittal sinus is replaced with an implant prosthesis ensuring physiological blood flow. The prosthesis is a cylindrical tubular member in which the end parts are provided with smooth, curvilinear, gently sloping bevels made on its internal generating surface or on both internal and external surfaces thereof.

The method is carried out in the following manner.

Trepanation and opening of the dura mater are carried out in the projection of the tumor location, in the form of bilateral semicircular incisions directed toward the base of the upper sagittal sinus. Free grafts of the dura mater are thrown toward each other. The veins running into the portion of the sagittal sinus to be removed are isolated from both sides, then the portion of the sagittal sinus is clipped sequentially above and below the tumor boundary. The tumor is removed as a single block together with a segment of the upper sagittal sinus and a portion of the faix cerebri. The removed segment of the upper sagittal sinus is replaced with an implant prosthesis.

Figure 1:
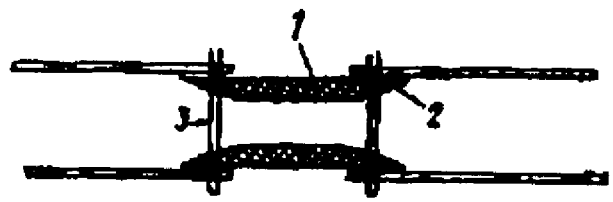
FIG. 1 is an elevated view of the prosthesis member according to the invention.

The prosthesis is a hollow tubular implant made from a biologically compatible plastic material used at present in the cardiovascular surgery. The end parts of the prosthesis (FIG. 1) are provided with smooth, curvilinear, gently sloping bevels made on Its internal generating surface, which ensure free passage of the blood flow and anti-thrombocyte properties. Prosthesis (1) is selected intraoperatively, it must enter sufficiently tightly into the upper- and lower-lying stump, and it is fixed with one or two silk or lavsan ligatures from both sides.

Figure 2:
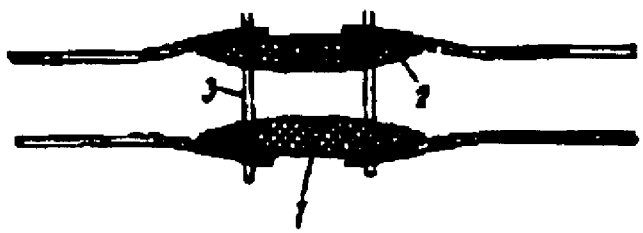
FIG. 2 is an elevated view of the prosthesis member according to the invention.

The end parts of the tubular prosthesis member can be provided with smooth, curvilinear, gently sloping bevels made on its internal and external surfaces (FIG. 2). In this case the implant prosthesis is inserted tightly into the upper- and lower-lying stump of the upper sagittal sinus, so that no thorough selection of the prosthesis is required.

It is necessary to have a set of tubular cylindrical members having a length ranging from 3 to 10 cm, with an inner diameter of 0.5 to 2 cm and an external diameter of 1 to 2.5 cm.

The proposed method for radical removal of a sagittal meningioma is novel, because it comprises not only total low-traumatic practically bloodless removal of the encephalonoma, but also restoration of the blood flow with the help of prosthetics.

The proposed method was approved experimentally under laboratory conditions in 1999.

A dog weighing 22 kg was operated upon under general anesthesia in accordance with the procedure set forth above. A portion of the USS was removed, and instead of it a prosthesis fixed from both ends with ligatures was implanted in the middle 3 cm long part thereof. The postoperative period was normal, without complications. The wound healing was primary, no pareses or paralyses were noted. The dog takes food freely, no aberrations in the animal's behavior are observed.

The proposed method is novel, because the reconstruction of the upper sagittal sinus with a view to restoring the physiological blood flow is achieved by creating an artificial portion of the upper sagittal sinus.

What is claimed is:

1. A process for radical removal of a parasagittal meningioma by carrying out trepanation and opening of the dura mater in the projection of tumor location, the method comprising the steps of:

making semicircular incisions of the dura mater;

circumscribing the tumor contour are made toward the base of the upper sagittal sinus; and removing the tumor as a single block together with a segment of the upper sagittal sinus and a portion of the faix cerebri, whereby the removed segment of the upper sagittal sinus is replaced with an implant prosthesis ensuring physiological blood flow.

2. A method according to claim 1, wherein the prosthesis is a hollow tubular cylindrical member in which the end parts are provided with smooth, curvilinear, gently sloping bevels made on its internal generating surface.

3. A method according to claim 1, wherein the prosthesis is a hollow tubular cylindrical member in which the end parts are provided with smooth, curvilinear, gently sloping bevels made on its external generating surface.

4. A method according to claim 1, wherein the prosthesis is a hollow tubular cylindrical member in which the end parts are provided with smooth, curvilinear, gently sloping bevels made on its internal and external generating surfaces.

* * * * *